(12) United States Patent
Roeder

(10) Patent No.: US 9,744,032 B2
(45) Date of Patent: Aug. 29, 2017

(54) ENDOLUMINAL PROSTHESIS COMPRISING A VALVE AND AN AXIALLY EXTENDABLE SEGMENT

(71) Applicant: COOK MEDICAL TECHNOLOGIES LLC, Bloomington, IN (US)

(72) Inventor: Blayne A. Roeder, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 293 days.

(21) Appl. No.: 13/793,726

(22) Filed: Mar. 11, 2013

(65) Prior Publication Data

US 2014/0257474 A1    Sep. 11, 2014

(51) Int. Cl.
| | | |
|---|---|---|
| A61F 2/24 | (2006.01) |
| A61F 2/82 | (2013.01) |
| A61F 2/04 | (2013.01) |
| A61F 2/07 | (2013.01) |

(52) U.S. Cl.
CPC .............. *A61F 2/2412* (2013.01); *A61F 2/04* (2013.01); *A61F 2/07* (2013.01)

(58) Field of Classification Search
CPC .................................. A61F 2/06; A61B 17/11
USPC ........ 623/1.11–1.2, 1.27–1.31; 606/153–156
See application file for complete search history.

(56) References Cited

U.S. PATENT DOCUMENTS

| | | | |
|---|---|---|---|
| 2003/0176911 A1* | 9/2003 | Iancea et al. ................. 623/1.13 |
| 2012/0158026 A1 | 6/2012 | Behan | |
| 2014/0243965 A1* | 8/2014 | Benson ................. A61F 2/2418 |
| | | | 623/2.18 |

FOREIGN PATENT DOCUMENTS

| | | |
|---|---|---|
| WO | WO2005/011535 | 2/2005 |
| WO | WO2011/109801 | 9/2011 |

OTHER PUBLICATIONS

Extended European Search Report for EP14275036 dated May 15, 2014, 7 pgs.
Response to Rule 69 EPC Communication filed Mar. 17, 2015 for European Patent Application No. 14275036.3, 18 pgs.

* cited by examiner

*Primary Examiner* — Yashita Sharma
(74) *Attorney, Agent, or Firm* — Brinks Gilson & Lione

(57) ABSTRACT

The present embodiments provide a prosthesis comprising first and second segments, and an axially extendable segment coupled to the first and second segments. A valve is coupled to at least one of the axially extendable segment or the second segment. The axially extendable segment comprises a first state in which the valve at least partially overlaps with the first segment, and the axially extendable segment comprises a second state in which the valve lacks an overlap with the first segment.

8 Claims, 5 Drawing Sheets

US 9,744,032 B2

ENDOLUMINAL PROSTHESIS COMPRISING A VALVE AND AN AXIALLY EXTENDABLE SEGMENT

BACKGROUND

The present embodiments relate to implantable medical devices and methods, and more particularly to an implantable medical device for the repair of a valve.

The aortic valve functions as a one-way valve between the heart and the rest of the body. Blood is pumped from the left ventricle of the heart, through the aortic valve, and into the aorta, which in turn supplies blood to the body. Between heart contractions the aortic valve closes, preventing blood from flowing backwards into the heart.

Damage to the aortic valve can occur from a congenital defect, the natural aging process, and from infection or scarring. Over time, calcium may build up around the aortic valve causing the valve not to open and close properly. Certain types of damage may cause the valve to "leak," resulting in "aortic insufficiency" or "aortic regurgitation." Aortic regurgitation causes extra workload for the heart, and can ultimately result in weakening of the heart muscle and eventual heart failure.

After the aortic valve becomes sufficiently damaged, the valve may need to be replaced to prevent heart failure and death. One current approach involves the use of a balloon-expandable stent to place an artificial valve at the site of the defective aortic valve. Another current approach involves the positioning of an artificial valve at the site of the aortic valve using a self-expanding stent. However, these techniques are imperfect. For example, the size of the implantation site depends on the unpredictable effects of a heavily calcified native valve and its annulus, and it may difficult for a self-expanding stent to seal within the annulus.

Further, balloon dilation of a stent at the site of the annulus may pose a problem when a valve is also implanted at the site of the annulus. In particular, balloon dilation of the stent at the site of the annulus may interfere with the valve and may compromise the functionality of the valve. Still further, when a balloon-expandable stent is loaded over a balloon in a delivery state, and the valve overlaps with the balloon-expandable stent, then the delivery profile of the system is increased by having the balloon, the stent, and the valve at the same axial location during delivery.

SUMMARY

The present embodiments provide a prosthesis comprising first and second segments, and an axially extendable segment coupled to the first and second segments. A valve is coupled to at least one of the axially extendable segment or the second segment. The axially extendable segment comprises a first state in which the valve at least partially overlaps with the first segment, and the axially extendable segment comprises a second state in which the valve lacks an overlap with the first segment.

The axially extendable segment may be secured to each of the first and second segments in both delivery and deployed states. A proximal end of the axially extendable segment may be coupled to a proximal end of the first segment, and a distal end of the axially extendable segment may be coupled to a proximal end of the second segment.

In one embodiment, the axially extendable segment comprises a plurality of first wire segments extending in a first direction and a plurality of second wire segments extending in a second direction, and the plurality of first wire segments intersect with the plurality of second wire segments. At least one fabric segment may be disposed between the first and second wire segments of the axially extendable segment.

The first segment may comprise a balloon-expandable stent, and the second segment may comprise a self-expandable stent. The second segment may comprise a graft coupled to a stent framework, and at least one fenestration may be provided in the graft of the second segment. The first and second segments may at least partially overlap with one another when the axially extendable segment is in the first state, and the first and second segments may lack an overlap with one another when the axially extendable segment is in the second state.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
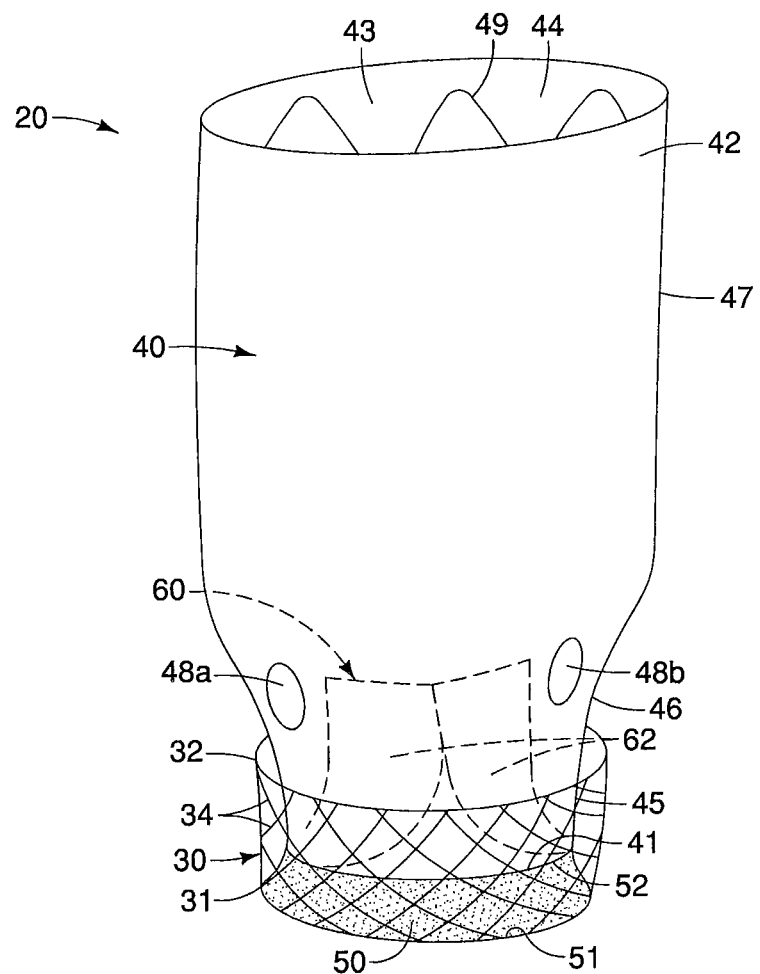
FIG. 1 is a side view of a first embodiment of an endoluminal prosthesis comprising a valve and an axially extendable segment.

Referring now to FIG. 1, a first embodiment of an endoluminal prosthesis 20 is shown and described. The prosthesis 20 generally comprises a first segment 30, a second segment 40, an axially extendable segment 50, and a valve 60.

The first segment 30 comprises a proximal end 31 and a distal end 32. In one embodiment, the first segment 30 comprises a balloon-expandable stent structure, as generally explained in the exemplary delivery and deployment discussion below. However, in alternative embodiments, the first segment 30 may comprise a self-expanding stent, which would preclude the need to have a balloon coupled to a delivery system as shown below.

For illustrative purposes to help differentiate components, the first segment 30 is depicted as having a framework of braided members 34 positioned between the proximal and distal ends 31 and 32. The braided members 34 are depicted solely for illustrative purposes and not intended to limit the structure of the stent framework of the first segment 30.

Figure 4A:
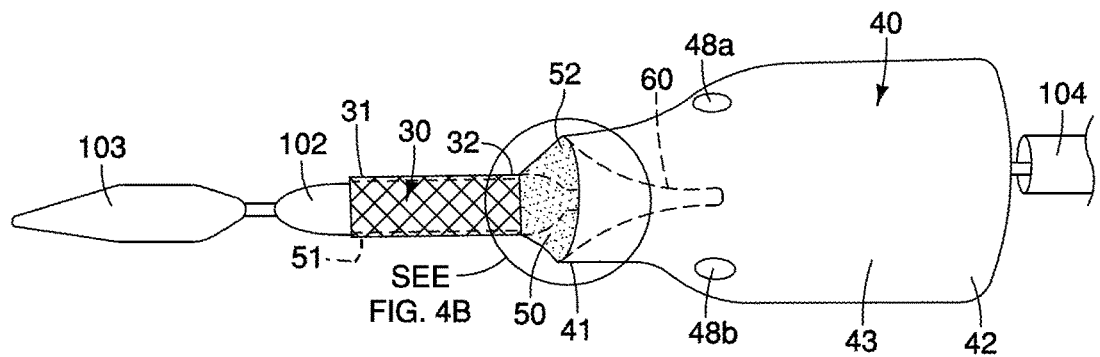
FIG. 4A is a side view illustrating a portion of the endoluminal prosthesis being coupled to the delivery system.

In alternative embodiments, several other stent structures may be used, so long as the framework can be reduced to a suitable delivery state, e.g., disposed around a balloon 102 as shown in FIG. 4A below, and further can be expanded to a suitable expanded state for applying a force upon a bodily space to anchor a portion of the prosthesis 20 in place. Optionally, one or more barbs may be coupled to the first segment 30 and oriented in directions that facilitate a secure engagement between the prosthesis and the bodily passage in which it is disposed.

At least a portion of the first segment 30 may comprise a covering that channels fluid flow into the valve 60. In one embodiment, the covering begins at the proximal end 31 of the first segment 30, which is coupled to the axially extendable segment 50, and extends distally at least to an area of the first segment 30 that seals with the vessel wall, such as the aortic annulus in the embodiment of FIG. 5. In certain embodiments, the entirety of the first segment 30 may comprise a covering to ensure that fluid is channeled into the valve 60.

The second segment 40 comprises a proximal end 41 and a distal end 42. In one embodiment, the second segment 40 comprises a self-expandable stent structure 49 coupled to a graft 43 having a lumen 44. In the example of FIG. 1, the stent structure 49 is depicted as comprising one or more zig-zag stents coupled to an interior surface of the graft 43. However, in alternative embodiments, the stent structure 49 may be coupled to the inside and/or outside of the graft 43 to enable self-expansion of the graft 43 to the expanded state, and may comprise shapes other than the zig-zag shape depicted.

In one embodiment, the stent structure 49 of the second segment 40 may be manufactured from a super-elastic material. Solely by way of example, the super-elastic material may comprise a shape-memory alloy, such as a nickel titanium alloy (nitinol). If the stent structure 49 of the second segment 40 comprises a self-expanding material such as nitinol, the stent may be heat-set into the desired expanded state, whereby the stent structure 49 can assume a relaxed configuration in which it assumes the preconfigured first expanded inner diameter upon application of a certain cold or hot medium. Alternatively, the stent structure 49 may be made from other metals and alloys that allow the stent structure to return to its original, expanded configuration upon deployment, without inducing a permanent strain on the material due to compression. Solely by way of example, the stent structure 49 may comprise other materials such as stainless steel, cobalt-chrome alloys, amorphous metals, tantalum, platinum, gold and titanium. The stent structure 49 also may be made from non-metallic materials, such as thermoplastics and other polymers.

Figure 5:
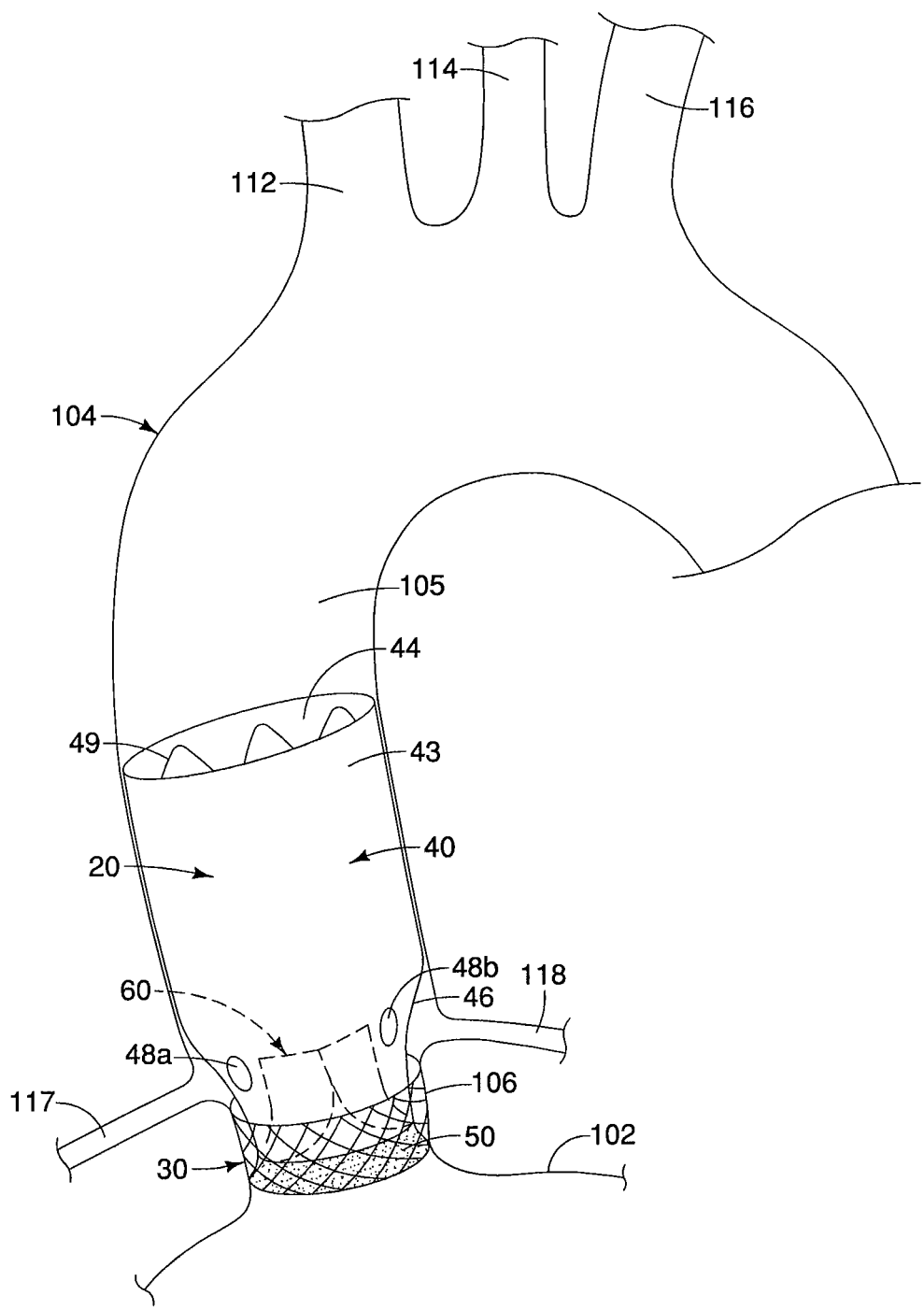
FIG. 5 is a schematic view of the endoluminal prosthesis of FIG. 1 being deployed during an aortic valve replacement procedure.

The second segment 40 further comprises a proximal region 45 having a first diameter, a distal region 47 having a second diameter, and a tapered region 46 disposed between the proximal and distal regions 45 and 46, as shown in FIG. 1. The second diameter of the distal region 47 may be greater than the first diameter of the proximal region 45. In one example, the proximal region 45 may be configured to be disposed at least partially within the aortic valve annulus, as shown in FIG. 5 below. By contrast, the distal region 47 comprises a generally cylindrical shape having an expanded outer diameter that is configured to be disposed at least partially within the ascending aorta. The tapered region 46 generally bridges the change from the first diameter to the second diameter.

In the example of FIG. 1, the prosthesis 20 comprises at least one fenestration 48 disposed in a sidewall of the graft 43 of the second segment 40. In the embodiment shown herein, first and second fenestrations 48a and 48b are disposed in the graft 43 at locations in the vicinity of the distal end of the valve 60, as depicted in FIG. 1.

The first and second fenestrations 48a and 48b may be provided in accordance with pivoting fenestrations described in detail in U.S. Patent Application Publication Number 2012/0046728, which is hereby incorporated by reference in its entirety. Accordingly, at least one of the fenestrations 48a and 48b is pivotable in any direction away from an axis perpendicular to a longitudinal axis of the prosthesis. In the non-limiting example of FIG. 1, the first and second fenestrations 48a and 48b are disposed in the graft 43 at locations between about 90 and about 270 degrees apart, though the positioning may be greater or less. In the deployed state, a first branch vessel prosthesis may extend between the first fenestration 48a and a first coronary artery 117 in a deployed state, and a second branch vessel prosthesis may extend between the second fenestration 48b and a second coronary artery 118, when the prosthesis is used to repair an aortic valve, as described in FIG. 5 below.

The axially extendable segment 50 may be positioned entirely or partially between the first and second segments 30 and 40. In one embodiment, the axially extendable segment 50 comprises a proximal end 51 that is coupled to the proximal end 31 of the first segment 30, as shown in FIG. 1. Further, the axially extendable segment 50 comprises a distal end 52 that is coupled to the proximal end 41 of the second segment 40, as shown in FIG. 1.

Figure 2:
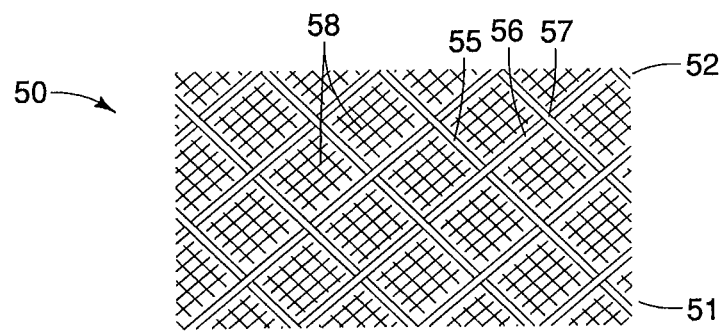
FIG. 2 is a side view illustrating features of the axially extendable segment of FIG. 1.

Referring to FIG. 2, further features of the axially extendable segment 50 are shown. In one non-limiting example, the axially extendable segment 50 comprises a braided portion comprising a plurality of first wire segments 55 extending in a first direction and a plurality of second wire segments 56 extending in a second direction. The plurality of first wire segments 55 intersect the plurality of second wire segments 56 at intersections 57, as shown in FIG. 2, to form the braided pattern. The first and second wire segments 55 and 56 may be movable with respect to one another to alter the amount of axial extension along a longitudinal axis L (see FIG. 3) of the prosthesis 20. In particular, the first and second wire segments 55 and 56 may move between an axially foreshortened state, as shown in FIG. 3, and an axially elongated state, as shown in FIG. 4.

Additionally, in the non-limiting example shown, one or more woven fabric segments 58 are provided between the first and second wire segments 55 and 56, as depicted in FIG. 2. The fabric segments 58 may comprise Dacron or another suitable material, which may provide suitable impermeability of the axially extendable segment 50 to ensure that fluid flows through the valve 60 in the deployed state, as depicted in FIG. 5 below. The fabric segments 58 may comprise a woven mesh of material that both provides suitable impermeability and flexibility to permit the first and second wire segments 55 and 56 to move between the axially foreshortened and extended states described in FIGS. 3-4 below.

In alternative embodiments, the axially extendable segment 50 may omit the first and second wire segments 55 and 56, and comprise other materials or support structures. For example, a flexible or stretchable biocompatible polymer material may be used, without a wire structure, which may provide suitable impermeability of the axially extendable segment 50 and also allow movement between the axially foreshortened and extended states shown herein.

Figure 6:
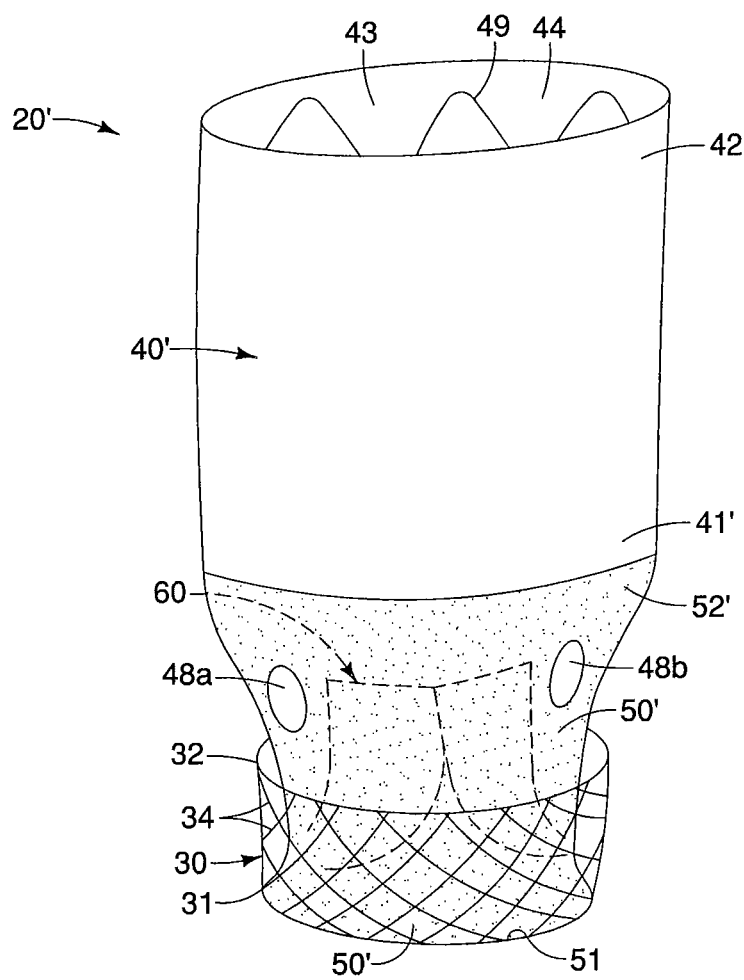
FIG. 6 is a side view of an alternative embodiment of an endoluminal prosthesis having a valve and an axially extendable segment.

The valve 60 of the prosthesis 20 is coupled to at least one of the axially extendable segment 50 or the second segment 40. In the example of FIG. 1, the valve 60 is coupled near the proximal end 41 of the second segment 40. The valve may alternatively, or additionally, be coupled to a portion of the axially extendable segment 50, for example, as shown in FIG. 6 below. The valve 60 may be coupled to the graft 43 of the second segment 40, and/or to the fabric segment 58 of the axially extendable segment 50, using a suitable technique such as suturing.

In one non-limiting example, the valve 60 may comprise an aortic valve designed to replace the function of the recipient's native damaged or poorly performing aortic valve, as explained further in FIG. 5 below. In other examples, the prosthesis 20 may be deployed in other arterial locations, i.e., other than the aortic valve annulus and ascending aorta, or alternatively may be deployed in a patient's venous system, or any suitable duct, passageway or vessel.

In the example of an aortic valve, the valve 60 preferably includes one or more leaflets 62, as shown in FIG. 1. For example, the valve 60 may include two leaflets 62 in a bicuspid arrangement, or three leaflets 62 may be used in a tricuspid arrangement. The leaflets are arranged in the prosthesis such that the leaflets mimic a naturally occurring aortic valve. The valve 60 "opens" to allow blood flow when the pressure on the proximal side of the valve 60 is greater than pressure on the distal side of the artificial valve. Thus, the valve 60 regulates the unidirectional flow of fluid from the heart into the aorta.

The leaflets of the valve 60 can be fabricated from any at least substantially biocompatible material including such materials as polyester fabrics, polytetrafluoroethylene (PTFE), expanded PTFE, and other synthetic materials known to those of skill in the art. Preferably, the leaflets are fabricated from naturally occurring biomaterials. The leaflets can include a derived collagen material, such as an extracellular matrix. The extracellular matrix can be small intestinal submucosa, stomach submucosa, pericardium, liver basement membrane, urinary bladder submucosa, tissue mucosa, dura mater, or the like.

As will be explained further below, in an expanded state of the prosthesis 20, shown in FIGS. 1, 3A and 5, at least a portion of the valve 60 overlaps with the first segment 30. Further, at least a portion of the second segment 40 may axially overlap with the first segment 30 in the expanded state. By contrast, in a delivery state of the prosthesis 20, shown in FIG. 4A, the valve 60 lacks an overlap with the first segment 30, and the second segment 40 also may lack an overlap with the first segment 30.

Referring now to FIGS. 3-4, a suitable delivery system 100 may be used to deliver and deploy the prosthesis 20 endoluminally. In one non-limiting example, the delivery system 100 comprises a catheter 101 having a balloon 102 disposed thereon, and the catheter 101 may comprise an atraumatic, tapered tip 103, as generally known in the art. Further, a sheath 104 may be dimensioned for longitudinal advancement with respect to the catheter 101.

Figure 3A:
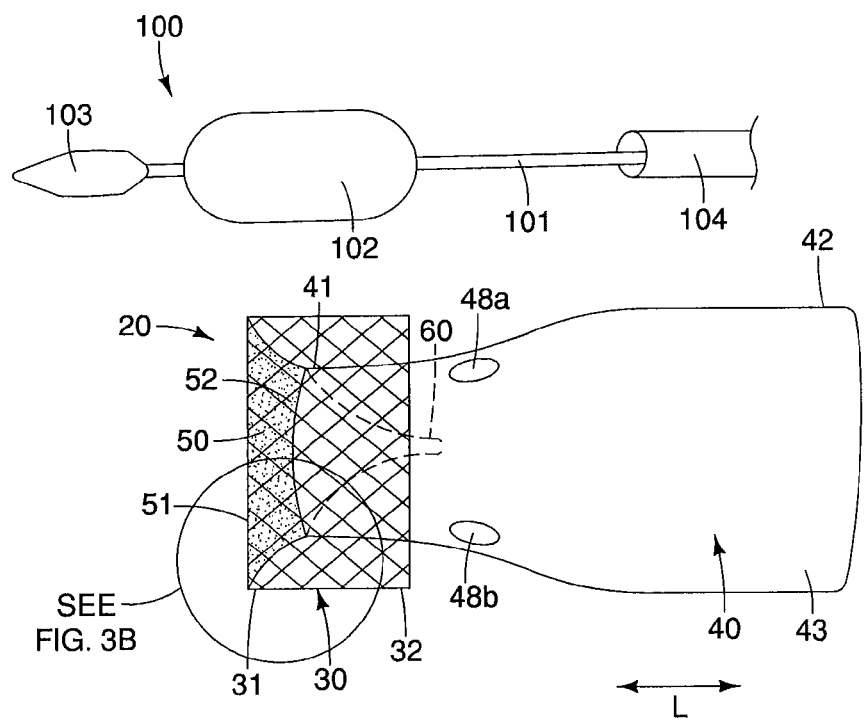
FIG. 3A is a side view illustrating a delivery system, and the endoluminal prosthesis prior to being coupled to the delivery system.
Figure 3B:
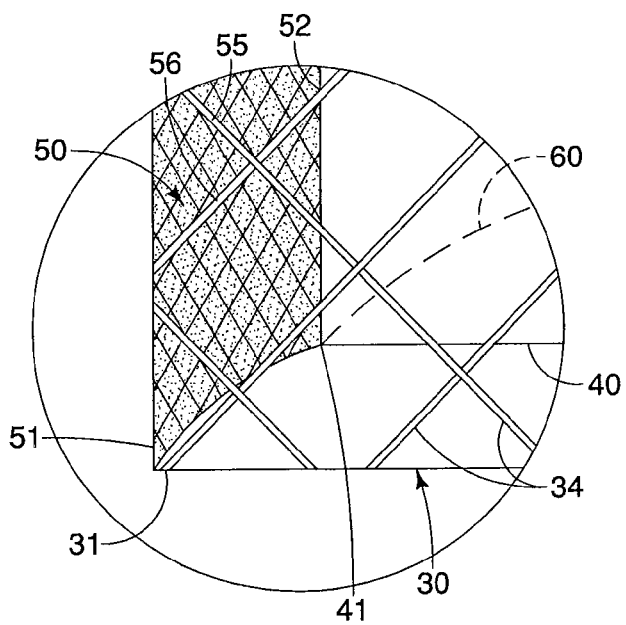
FIG. 3B is an enlarged side view of FIG. 3A, illustrating a portion of the axially extendable segment in a first state.
Figure 4B:
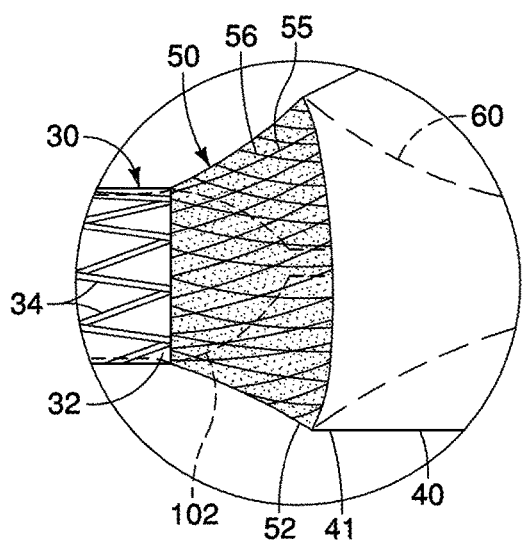
FIG. 4B is an enlarged side view of FIG. 4A, illustrating a portion of the axially extendable segment in a second state.

The prosthesis 20 may be coaxially aligned over the catheter 101 when in the expanded state shown in FIG. 3A. In particular, the first segment 30 may be disposed over the balloon 102. As noted above, in this expanded state, at least a portion of the valve 60 and the second segment 40 may overlap with the first segment 30, as shown in FIG. 3A.

Prior to being secured to the delivery system 100, the prosthesis is moved from a first state shown in FIG. 3A to a second state shown in FIG. 4A. In the second state, the second segment 40 of the prosthesis and the valve 60 are distally advanced with respect to the first segment 30, along the longitudinal axis L. In the second state, the second segment 40 and the valve 60 lack an overlap with respect to the first segment 30, as shown in FIG. 4A.

It should be noted that the axially extendable segment 50 becomes longitudinally elongated to permit the distal advancement of the second segment 40 and the valve 50 with respect to the first segment 30. In the example shown herein, in which the axially extendable segment 50 comprises a braided portion, the orientation of the plurality of first and second wire segments 55 and 56 change with respect to the longitudinal axis L of the prosthesis 20, e.g., moving from the foreshortened orientation of FIG. 3B to the elongated orientation of FIG. 4B. In particular, the first and second wire segments 55 and 56 move from an orientation that is more perpendicular to the longitudinal axis L in FIG. 3B to an orientation that is more parallel to the longitudinal axis L in FIG. 4B.

While in the second state of FIG. 4A, the first segment 30 may be crimped securely around the balloon 102 to a reduced diameter delivery state. Advantageously, at this time, the valve 60 is not disposed within the first segment 30, or in any way overlapping the first segment 30, and is therefore not subjected to the potentially damaging crimping forces required to hold the first segment 30 around the balloon 102. As a further advantage, since the second segment 40 and the valve 60 may lack an overlap with the first segment 30 and the balloon 102, a staggered positioning of components may be achieved that may significantly reduce the delivery profile of the system.

The sheath 104 is positioned during delivery so that is covers each segment of the prosthesis 20 in the delivery state, thereby radially restraining the second segment 40 and any associated self-expanding stents. The delivery system 100, with the endoluminal prosthesis 20 secured thereto, then is delivered to a target site, such as the ascending aorta, as described further in FIG. 5 below.

Upon delivery at the target site, the sheath 104 may be partially distally withdrawn to expose the first segment 30. The balloon 102 then is inflated to radially deploy the first segment 30 into engagement with target tissue. Advantageously, since the valve 60 is not disposed within the first segment 30 when the first segment 30 is expanded by the balloon 102, the valve 60 is therefore not subjected to the potentially damaging forces caused by expansion of the balloon 102.

With the first segment 30 having been deployed to a radially enlarged state by the balloon 102, the balloon 102 may be deflated. The sheath 104 then may be retracted to expose the axially extendable segment 50, which will be inclined to return to its foreshortened orientation, in which it is disposed within a portion of the first segment 30. At this time, foreshortening of the axially extendable segment 50 may pull the second segment 40 proximally to at least partially overlap within the first segment 30. If needed, the catheter 101 and/or the sheath 104 may be manipulated to proximally advance the axially expandable segment 50 and the second segment 40 such that they once again overlap within the first segment 30. The sheath 104 then may be proximally retracted to allow the second segment 40 to self-expand to the deployed state shown in FIGS. 1, 3A and 5, in which the valve 60 overlaps within a portion of the first segment 30.

Referring now to FIG. 5, further details of an aortic deployment are explained with regard to the non-limiting example where the valve 60 comprises an aortic valve replacement. A partial cut-away view of a heart 102 and an aorta 104 are shown. The heart 102 may comprise an aortic valve that does not seal properly. This defect of the aortic valve allows blood to flow from the aorta 104 back into the left ventricle, leading to a disorder known as aortic regurgitation. Also shown in FIG. 5 are a brachiocephalic trunk 112, a left common carotid artery 114, and a left subclavian artery 116. A portion of the aorta 104 referred to herein as an ascending aorta 105 is shown located between the aortic valve annulus 106 and the brachiocephalic trunk 112. A patient's coronary arteries 117 and 118 are located distal to the aortic valve annulus 106.

The prosthesis 20 may be configured and sized for endoluminal delivery and deployment through a femoral cut-down. The prosthesis 20 may be secured to the delivery system 100 of FIGS. 3-4, in a manner such that the valve 60 and the second segment 40 lack an overlap with the first segment 30 and the balloon 102, as explained in FIG. 4A above. In addition to the delivery system 100 of FIGS. 3-4, various other components may need to be provided in order to obtain a delivery and deployment system that is optimally suited for its intended purpose. These include and are not limited to various outer sheaths, pushers, trigger wires, stoppers, wire guides, and the like. For example, the Zenith® Thoracic Aortic Aneurysm Endovascular Graft uses a delivery system that is commercially available from Cook Inc., Bloomington, Ind., and may be suitable for delivering and deploying an aortic prosthesis in accordance with the present embodiments.

Upon deployment, the prosthesis 20 is positioned as generally shown in FIG. 5. When the prosthesis 20 is implanted, sufficient flow into the coronary arteries 117 and 118 is maintained during retrograde flow. In particular, after blood flows through the distal region of the valve 60, blood is allowed to flow adjacent to the outside of the valve 60 and into the coronary arteries 117 and 118, i.e., through the fenestrations 48a and 48b in the graft 43.

Further, if barbs are disposed along the proximal segment 30, the barbs may promote a secure engagement with the aortic valve annulus 106. Similarly, barbs may be secured to the second segment 40 to promote a secure engagement with the ascending aorta 105. In the event barbs are omitted, the first and second segments 30 and 40 may be configured so that the radial forces exerted upon the aortic valve annulus 106 and the ascending aorta 105, respectively, are enough to hold the prosthesis 20 in place.

The shape, size, and dimensions of each of the members of the prosthesis 20 may vary. The size of a preferred prosthetic device is determined primarily by the diameter of the vessel lumen (preferably for a healthy valve/lumen combination) at the intended implant site, as well as the desired length of the overall stent and valve device. Thus, an initial assessment of the location of the natural aortic valve in the patient is determinative of several aspects of the prosthetic design. For example, the location of the natural aortic valve in the patient will determine the dimensions of the segments 30, 40 and 50 and the valve 60, along with the type of valve material selected, and the size of deployment vehicle.

After implantation, the valve 60 replaces the function of the recipient's native damaged or poorly performing aortic valve. The valve 60 allows blood flow when the pressure on the proximal side of the valve 60 is greater than pressure on the distal side of the valve. Thus, the valve 60 regulates the unidirectional flow of fluid from the heart into the aorta.

As noted above, while one exemplary use of the prosthesis 20 has been shown with regard to the aortic valve annulus and ascending aorta, the prosthesis 20 alternatively may be deployed in other parts of a patient's arterial or venous system, or any suitable duct, passageway or vessel.

Referring to FIG. 6, in an alternative embodiment, a prosthesis 20' is substantially identical to the prosthesis 20 of FIGS. 1-5, with an exception that an alternative axially extendable segment 50' extends further distally to replace the proximal segment 45 and the tapered portion 46 of an alternative second segment 40'. In this embodiment, an alternative distal end 52' of the axially extendable segment 50' is coupled to an alternative proximal end 41' of the second segment 40' at a location further distally as compared to the embodiment of FIG. 1. Further, in the embodiment of FIG. 6, the alternative axially extendable segment 50' may be coupled to the valve 60, and may comprise the fenestrations 48a and 48b. The embodiment of FIG. 6 may provide added flexibility to the prosthesis 20' in the regions near the fenestrations 48a and 48b, which may provide added axial flexibility when placing bridging stents between the fenestrations 48a and 48b and branch vessels of a patient.

In a further alternative embodiment, the second segment 40 may be omitted, and an alternative prosthesis comprising only the first segment 30, the axially extendable segment 50 and the valve 60 may be provided. In this example, the valve 60 may be positioned to lack an overlap with the first segment 30 during delivery, via expansion of the axially extendable segment 50, as generally explained above. Further, by omitting the second segment 40, the alternative prosthesis may be capable of percutaneous delivery into substantially small vessels of a patient.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A prosthesis, comprising:
   a first segment having a proximal end and a distal end;
   a second segment having a proximal end and a distal end;
   an axially extendable segment having a proximal end and a distal end and coupled to the first and second segments, the axially extendable segment having a first state in which the first and second segments at least partially overlap with one another, and a second state in which the first and second segments lack an overlap and in which the first segment is located proximal to the second segment; and
   a valve coupled to at least one of the axially extendable segment or the second segment,
   wherein the proximal end of the axially extendable segment is coupled to the proximal end of the first segment and wherein the distal end of the axially extendable segment is coupled to the proximal end of the second segment.

2. The prosthesis of claim 1, wherein the axially extendable segment is secured to each of the first and second segments in both delivery and deployed states.

3. The prosthesis of claim 1, wherein the axially extendable segment comprises a plurality of first wire segments extending in a first direction and a plurality of second wire segments extending in a second direction, wherein the plurality of first wire segments intersect with the plurality of second wire segments.

4. The prosthesis of claim 3, further comprising at least one fabric segment disposed between the first and second wire segments of the axially extendable segment.

5. The prosthesis of claim 1, wherein the first segment comprises a balloon-expandable stent.

6. The prosthesis of claim 1, wherein the second segment comprises a self-expandable stent.

7. The prosthesis of claim 1, wherein when the axially extendable segment is in the second state, a distal diameter of the second segment is larger than a proximal diameter of the first segment.

8. The prosthesis of claim 1, wherein when the axially extendable segment is in the first state, the first segment partially surrounds the second segment.

* * * * *